United States Patent
Chen

(10) Patent No.: US 6,502,456 B1
(45) Date of Patent: Jan. 7, 2003

(54) METHOD AND APPARATUS FOR MEASURING MULTIPLE PARAMETERS OF STEAM

(75) Inventor: Yaosheng Chen, Blacksburg, VA (US)

(73) Assignee: Photosonic, Inc., Blacksburg, VA (US)

( * ) Notice: Subject to any disclaimer, the term of this patent is extended or adjusted under 35 U.S.C. 154(b) by 0 days.

(21) Appl. No.: 09/255,846

(22) Filed: Feb. 23, 1999

(51) Int. Cl.$^7$ .......................... E21B 44/00; E21B 47/00; G01N 7/00
(52) U.S. Cl. ................... 73/152.46; 73/152.01; 73/29.01
(58) Field of Search .................. 73/152.46, 29.01, 73/861.04, 152.27, 152.01; 166/250, 252; 374/42, 45

(56) References Cited

U.S. PATENT DOCUMENTS

| | | | |
|---|---|---|---|
| 4,149,403 A | * | 4/1979 | Muldary et al. ............ 73/29.01 |
| 4,409,825 A | * | 10/1983 | Martin et al. ............ 73/152.27 |
| 4,542,993 A | | 9/1985 | Mims |
| 4,712,006 A | * | 12/1987 | Zemel et al. ............. 250/269.3 |
| 4,876,897 A | * | 10/1989 | DeCarlo et al. ......... 73/861.04 |
| 5,031,465 A | | 7/1991 | Redus |
| 5,404,745 A | | 4/1995 | Chien |
| 5,709,468 A | | 1/1998 | Woerheide et al. |
| 5,710,717 A | | 1/1998 | Hong |
| 5,731,517 A | | 3/1998 | Ma et al. |

OTHER PUBLICATIONS

Author: R. Kerr, "How to Measure Downhole Steam Quality Using a Thermocouple and a Non–Condensible Gas," Journal of Canadian Petroleum Technology, vol. 38. No. 4 p. 27–30, 1999 Note: Steam quality = Steam aridity.

* cited by examiner

Primary Examiner—Hezron Williams
Assistant Examiner—Jay Politzer
(74) Attorney, Agent, or Firm—Stevens, Davis, Miller, & Mosher, LLP

(57) ABSTRACT

A method and an apparatus are disclosed for the measurement of the aridity, temperature, flow rate, total pressure, still pressure, and kinetic pressure of steam at a downhole location within a well through which wet steam is flowing. The apparatus comprises a series of fiber optic sensors that are mounted on sections of a shell assembly. The apparatus is lowered into a well to different downhole locations, and measures the multiple parameters of steam at different locations and heights. The data can be stored on board for subsequent analysis at the surface when the apparatus is retrieved from the well. The apparatus is very reliable, accurate, and of long-life in harsh environments.

23 Claims, 4 Drawing Sheets

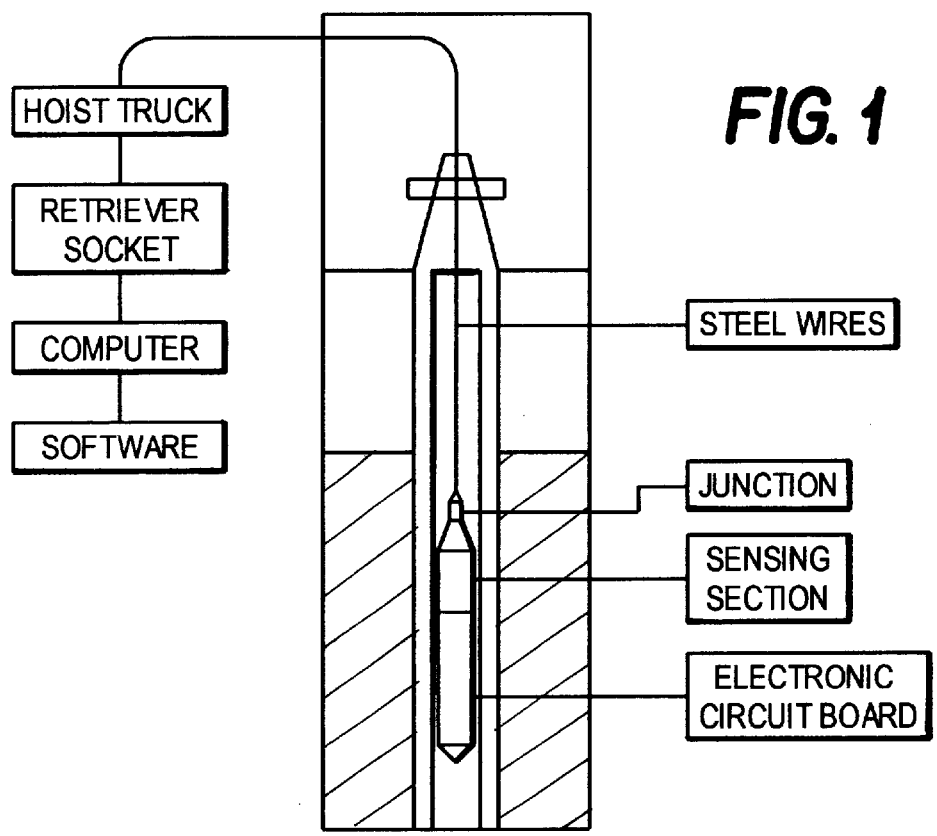
FIG. 1
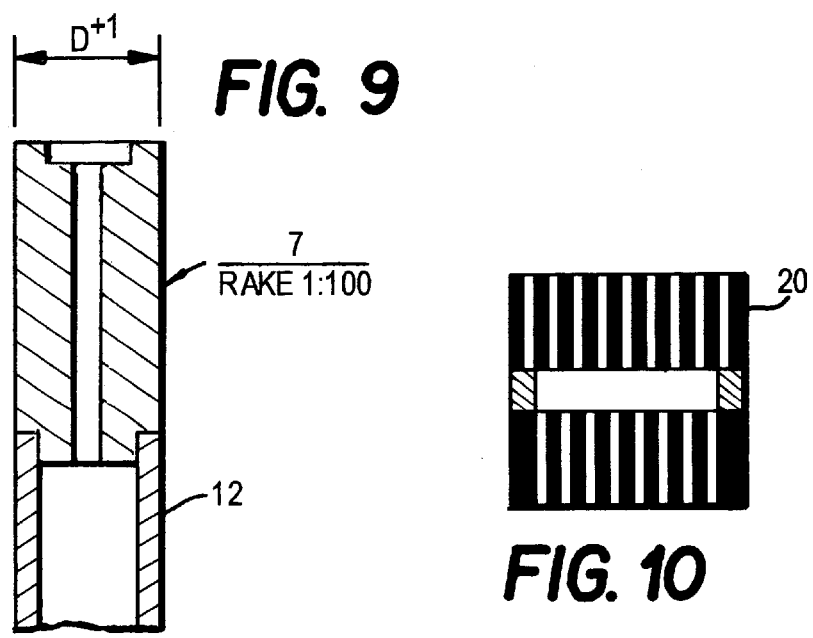
FIG. 9
FIG. 10

$\Phi - D = 8-12 \text{(mm)}$ $\delta = 0.2-0.5 \text{(mm)}$

VACUUM

HEAT INSULATION MATERIAL $\delta = 0.2-0.5 \text{(mm)}$ $D - d = 16-20 \text{(mm)}$

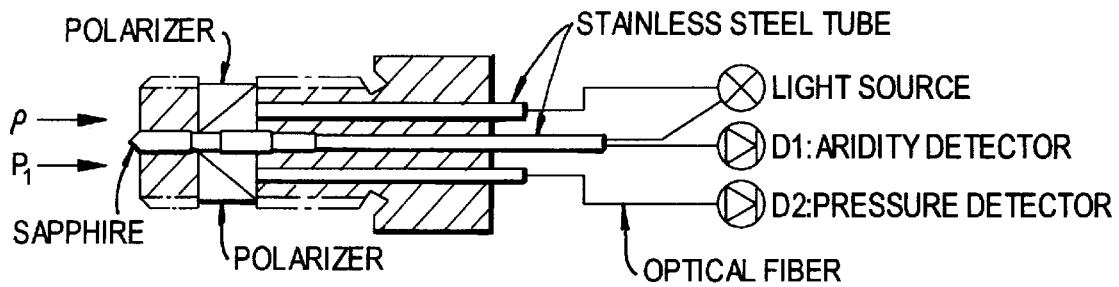
FIG. 4(a)  $\frac{A-M}{19}$
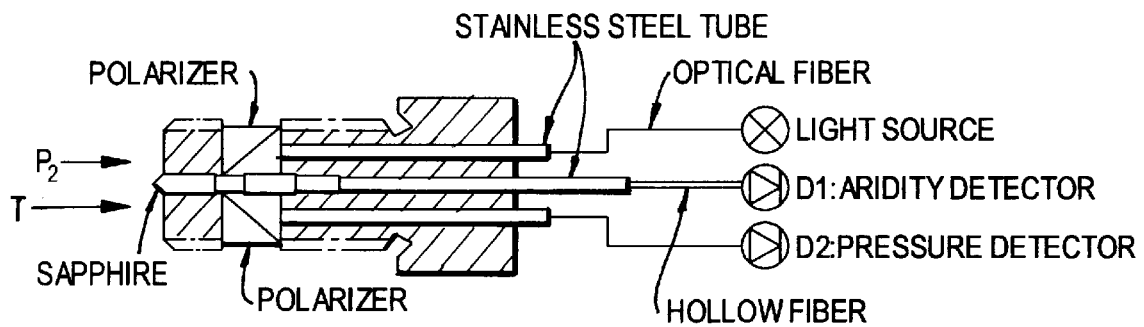
FIG. 4(b)  $\frac{B-M}{19}$
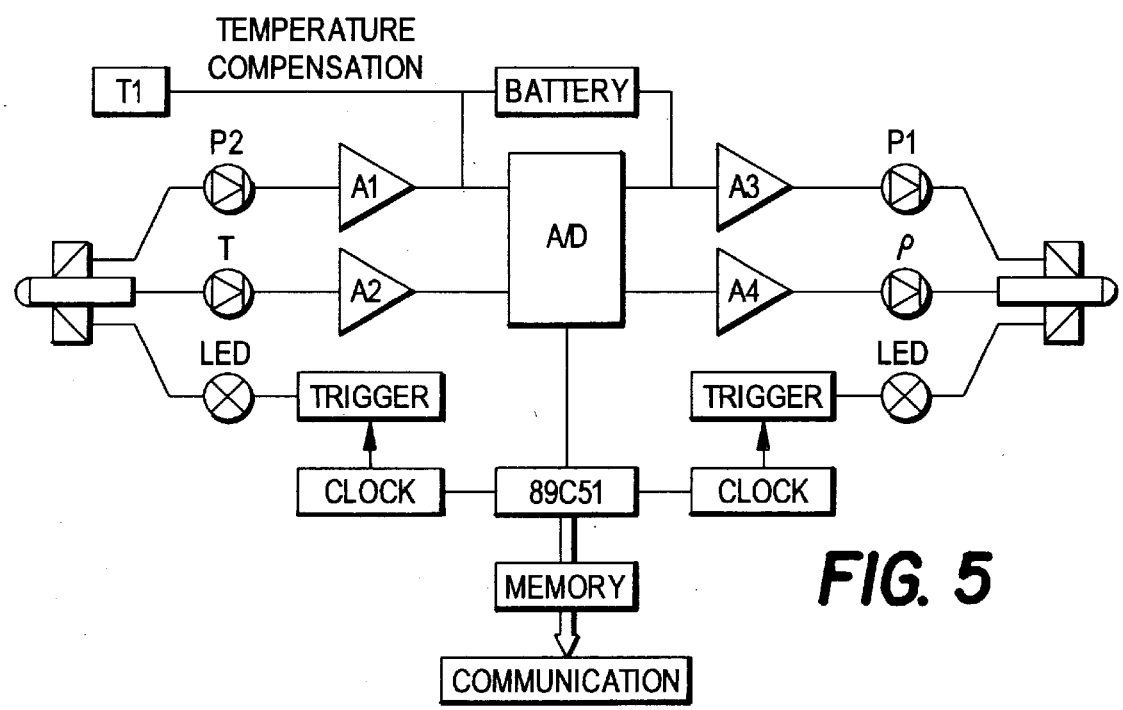
FIG. 5

METHOD AND APPARATUS FOR MEASURING MULTIPLE PARAMETERS OF STEAM

BACKGROUND—FIELD OF INVENTION

The present invention relates generally to a method and an apparatus for measuring the aridity, temperature, flow rate, total pressure, still pressure, and kinetic pressure of steam at a downhole location within a well through which wet steam is flowing.

BACKGROUND PRIOR ART

In the exploration and production of crude oil, it is often found that the crude oil is too viscous to be recovered, so in many cases, saturated steam has to be injected into the petroleum wells to dilute and force the thick oil out of the downhole wells, thus these wells are called steam injection wells. It is estimated that as much as two thirds of the oil in existing reservoirs cannot be recovered, due to difficulties in measuring downhole environmental conditions. However, the cost of generating and maintaining the steam to recovering the crude oil deposits accounts for a high percentage of the total cost of well operation, and the equivalent of as much as one-third of the total crude oil recovered is required to produce the steam that is required for the recovery process. Therefore, any technique that allows the operator to utilize the steam more efficiently will be useful.

On the other hand, geothermal energy has been used directly for the generation of electricity. Hot water, at a temperature from 140° C. to more than 300° C. is brought from an underground reservoir to the surface through production wells. Sensing, communication and process control have become commonplace functions during geothermal well drillings.

The measurement of multiple parameters, i.e. aridity, temperature, fluid-flow, still pressure, total pressure, and kinetic pressure of steam, allows the determination of factors affecting the production yield of oil recovery, the consumption of energy, and information concerning the oil reservoirs. Very precise measurements of physical parameters during geothermal well drillings are also highly required in many applications. However, instruments to be used for these measurements and processes must be able to survive in such harsh environments, at high temperature of 400° C. and high pressures of 20 MPa or more.

Currently available electrical cables and optical fiber cables cannot directly withstand such high temperatures because their cabling and jacketing materials would be melted immediately. Additionally, the wall of an instrumentation apparatus housing must be sufficiently thick to withstand the high pressure in downhole wells. The combined effects of high temperature and pressure make the fabrication of the sensing apparatus even more difficult, because they may cause high stress on the materials, which may result in inaccurate measurements.

Previously, no apparatus or method has yet been successfully developed for the measurement of even one parameter, except fluid-flow, in steam injection wells, even though great efforts have been attempted. Several approaches have been proposed for the measurement of steam pressure and temperature. One example is that of temperature measurement with a thermocouple, and the use of a hydraulic pressure gauge or other sensor to determine the pressure. Because the boiling points of most working media are below 350° C., and the temperature of saturated steam is 400° C., this approach has significant difficulties. Another example is the "spinner" flowmeter. However, the spinner flowmeter has a minimum flow velocity sensitivity of about 2 to 4 feet/minute in wells of 4-inch or larger diameter and is not capable of measuring slow fluid flows.

The present invention is a milestone development in apparatus and methods for performing quantitative measurements of the physical properties of steam in harsh environments. Combined with the measurement of two-phase flow properties, it offers a new method and apparatus to directly measure and record aridity, temperature, fluid-flow rate, total pressure, still pressure, and kinetic pressure of steam simultaneously in steam injection wells and in geothermal well drillings. Field tests have demonstrated very promising and exciting results with the high accuracy and reliability that has been impossible in the past.

OBJECTS AND ADVANTAGES

Accordingly, it is an object of the present invention to provide a method and an apparatus that are capable of measuring the aridity, temperature, fluid-flow rate, total pressure, kinetic pressure, and still pressure of steam in a high-temperature and high-pressure environment with accuracy and reliability.

It is another object of the present invention to provide a method and an apparatus that are capable of measuring the aridity, temperature, fluid-flow rate, total pressure, kinetic pressure, and still pressure of steam at high-temperature and high-pressure within a downhole well, such as a steam injection well or a geothermal production well, with accuracy and reliability.

It is a further object of the present invention to provide a method and an apparatus that are capable of measuring the aridity, temperature, fluid-flow rate, total pressure, kinetic pressure and still pressure of steam flowing inside a steam pipe with accuracy and reliability.

Objects of the present invention are achieved by providing a sensing apparatus that includes a combination of several fiber optic sensors having metal shell-housings and heat insulation means that protect said fiber optic sensors on an interconnected electronic circuit board, and allow their survival and proper operation the harsh high-temperature and high-pressure environments.

The apparatus of the present invention provides many advantages. First, the apparatus directly measures and stores the data necessary to determine multiple engineering parameters associated with the steam in a well. Second, many multi-parameter measurements may be obtained each time the apparatus is inserted into and withdrawn from the well, allowing comparison between measured data to insure valid data, and to obtain information concerning the variation in the properties of the steam at different height positions in the well. Additionally, said steam properties at different locations within the well and different temperatures, pressures, aridities and flow rates may be obtained and combined to determine the state and the state changes of the single phase or multi-phase well steam. Moreover, a specially designed shell and heat insulation mechanism keep the temperature inside the apparatus below 80° C., which allows the multiple-parameter measurements to be made with high accuracy and reliability, so the apparatus can be used for a very long time.

BRIEF DESCRIPTION OF THE DRAWINGS

FIG. 1 is a pictorial view of the downhole sensor apparatus construction. The entire sensor is first lowered into a FIG. 2 is a sectional view of the sensing part of the apparatus.

FIG. 4(a) shows a schematic diagram of the aridity and the total pressure sensing part of the apparatus.

FIG. 4(b) shows a schematic diagram of the temperature and the still pressure sensing part of the apparatus.

FIG. 5 shows a schematic block diagram of the electronic circuit inside the apparatus.

FIG. 9 shows a bottle stopper.

FIG. 10 shows a buffer grating.

Figure 2:
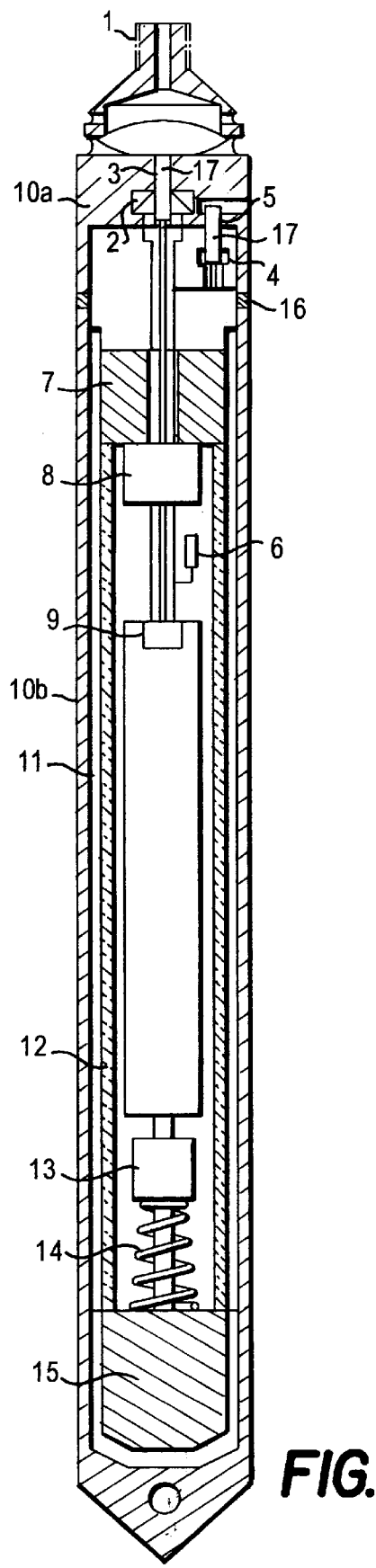

REFERENCE NUMERALS IN DRAWINGS 1. retriever head
2. total pressure sensor (P1)
3. aridity sensor ($\rho$)
4. still pressure sensor (P2)
5. temperature sensor (T)
6. temperature compensation element T1
7. flask stopper
8. retriever socket
9. electronic circuit board
10a. front shell
10b. back shell
11. thermal insulation flask
12. evenly distributed thermal tube
13. battery
14. spring
15. thermal insulation material
16. spacer
17. sensing element
18. base I
19. A-M: the aridity sensor and the total pressure sensor; B-M: the still pressure sensor and temperature sensor
20. buffer grid

DESCRIPTION OF THE PREFERED EMBODIMENT

The present invention is a significant development in fiber optic sensors, apparatus, and methods for performing quantitative measurements of the aridity, temperature, fluid-flow rate, total pressure, still pressure, and kinetic pressure of steam in harsh environments. It is not practical to approximate or simulate the conditions of high-temperature and high-pressure since there is no physical law available that can be used to explain such conditions. Here an empirical formula is employed:

$$P = P1 - P2 \quad (1)$$

$$-P = (1/2)\rho v^2 \quad (2)$$

Where P is the kinetic pressure, P1 is the total pressure, P2 is the still pressure, $\rho$ is the aridity or steam density, and v is the flow rate of the steam. As steam moves inside transmission pipes, the pressure measured is the total pressure, which includes both still pressure and kinetic pressure, whereas when the steam does not move, the pressure measured is the still pressure.

For a general understanding of the present invention, reference will now be made in detail to the present preferred embodiments shown in the drawings.

Since the steam may flow at a temperature of 400° C. or more, and at pressure of 20 MPa or more, there are no commercially available optic fibers or electrical cables able to withstand such a harsh environment. Thus the lowering-down and retrieving-back of the test instrument using steel wires or cables has proven to be the most feasible and appropriate method to obtain downhole steam well data to date.

FIG. 1 is a pictorial view of an entire system constructed in accordance with the present invention; said whole system comprising Junction. The joint between the steel wires and a test apparatus. The steel wires are used to lower and retrieve the apparatus into and out of a well. The junction is specially designed for the easy recovery of the apparatus if the steel wires are broken accidentally.

Sensing section. The core part of the entire assembly. It performs the measurement of the aridity, temperature, fluid-flow, total pressure, still pressure, and kinetic pressure of the steam and can run continuously for more than 8 hours at high-temperature and high-pressure. The temperature is maintained at less than 80° C. inside the shell.

Electronic circuit section. It comprises a power supply, an electronic circuit board and a processor used for data acquisition and storage.

Hoist truck. It provides the mechanical power to lower and lift the steel wires and the apparatus into and out of a downhole well.

Communication data port. An RS-232 standard Driver/Receiver, in which TTL/CMOS signal levels are transformed into RS-232 signals.

Computer. It is used to access information from the electronic circuit for data processing, displaying, printing, and storage through the use of internal software.

FIG. 2 is a sectional view of the test apparatus. Referring to the figure, a multiple-parameter measuring apparatus comprises a retriever head 1, which provides a means to connect the apparatus and the steel wires and to recover the apparatus if the steel wires are broken. A sensor 2 used for the measurement of total pressure P1, and a sensor 3 employed for the measurement of the aridity $\rho$, are mounted along the central axis line, a sensor 4 for the measurement of the still pressure P2 is fixed inside a blind hole, and a sensor 5 for the measurement of temperature T is assembled near said sensor 4, a thermal insulation flask 11 is typically made of polished metal sheets and sealed inside a front shell 10a, and said front shell 10a is typically made of a stainless steel. An evenly distributed thermal tube 12 is inserted into said thermal insulation flask 11, and all five sensors are placed inside said evenly distributed thermal tube 12. An element 6 for temperature compensation T1 is also assembled inside the evenly distributed thermal tube 12, and is used for the correction of the measurement errors obtained inside the evenly distributed thermal tube 12. Eight pieces of optical fiber for the five sensors and said temperature compensation element 6 go through a flask stopper 7, and a retriever socket 8, and are connected to an electronic circuit board 9. There is a hole of about 5 mm in diameter that allows the optical fiber passage on said retriever socket 8. Said electronic circuit board 9 is connected to a power socket, and a battery 13 provides the power. When said battery 13 needs to be replaced, the evenly distributed thermal tube 12 is removed, and the battery 13 is changed.

A spring 14, a thermal insulation material 15, a back shell 10b, and the thermal insulation flask 11 are assembled together. When the apparatus is retrieved back from the downhole well after data collection and storage, the assembly may be opened by twisting the spacer 16, separating the front shell and the back shell, and allowing said retriever socket 8 to be exposed, and then connecting the retriever socket 8 to a computer to allow data transfer. All the outer parts of the testing instrument are welded tightly except said spacer 16 in order to prevent steam or other leakage at a pressure of 25 MPa and a temperature of 400° C.

Figure 3:
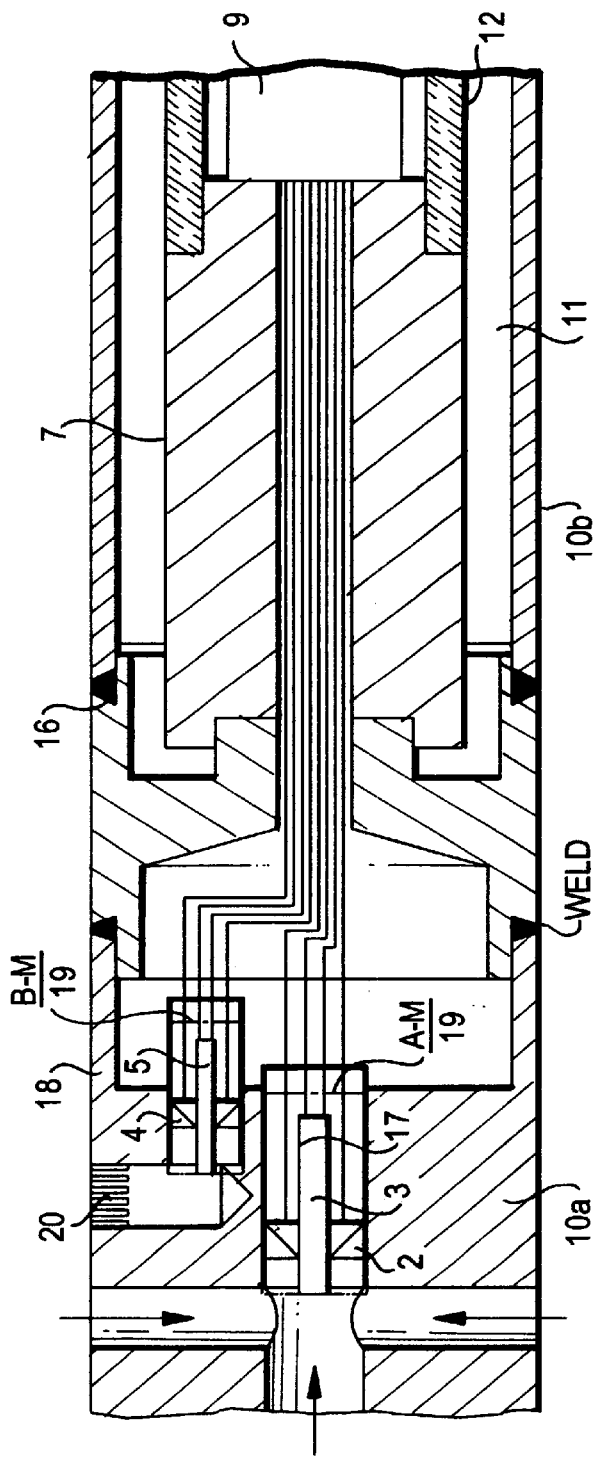
FIG. 3 is a graphical representation of the sensing apparatus.

FIG. 3 shows the inner structure of the sensing apparatus. A sensing element 17 is typically made of sapphire or ruby or other appropriate crystal material that is sensitive to aridity, pressure and temperature. There are two pieces of said sensing elements 17; one used for sensors 2 and 3, the other for sensors 4 and 5. One preferred embodiment is that of a sapphire element that has a taper of 1:20, the length of the sapphire being about 20 mm, the diameter of the small end being 2 mm, and the diameter of the large end being 3 mm. Both of the end surfaces are polished. For the sensors 2 and 3, the large end is polished into an ellipsoidal shape and the distance between the two focuses of the ellipsoid is about 420 μm. The two focuses of the ellipsoid should have high concentricity with the input and output optic fibers. The tapered sensing element 17 with its larger end oriented toward the steam is mounted on a base 18. Said base 18 is mounted on the front shell 10a with threads. For sensors 4 and 5, the large end is polished into a spherical shape with a diameter of 3 mm, and mounted on a base 18 with its larger end oriented toward the steam. A specially designed buffer grid 20 is mounted on the front shell 10a in order to keep the steam inside the hole motionless for the purpose of the measurement of the still pressure P2. Under a pressure P, strain inside the specially shaped and dimensional crystal is created and this results in an induced birefringence, i.e.

$$\Delta n = n_0 - n_e = kP, \quad (3)$$

Where k is the strain-induced birefringence constant. Therefore, the birefringence difference Δn is proportional to the pressure P. If the diameter of the sensing element is "1", the optical path difference is given by $$\Delta = (n_0 - n_e) 1 = kP1, \quad (4)$$

and the resulting phase difference can be written $$\Delta\phi = 2\pi/\lambda (n_0 - n_e) 1 = 2\pi k P 1/\lambda. \quad (5)$$

Thus, the output light intensity is given by $$I = I_0 \sin 2(\pi k P 1/\lambda). \quad (6)$$

Therefore, the total pressure P1 can be obtained by the sensor 2, and the still pressure P2 is obtained by the sensor 4 at the same time, using this specially shaped and dimensional cyrstal.

Thus, the flow rate v can be given by $$v^2 = 2(P1 - P2)/\rho. \quad (7)$$

From A-M in FIG. 4(a), sensor 2 (the total pressure P1) and sensor 3 (the aridity ρ) are grouped together and share a light source, for example, a light emitting diode (LED). Two pieces of optical fiber with diameters of about 300 μm are connected to the small end of the first sensing element 17, one is used to transmit light from said light source, the other is used to transmit light modulated by aridity changes from the sensing element to the photoelectric converter. A conventional photoelectric converter is used to detect the aridity signal. Another two pieces of optical fiber are employed to measure pressure; one fiber to transmit light from the same light source to said first sensing element 17 through a polarizer; another to transmit light from the sensing element through a second polarizer and to a separate photoelectric converter. The output signal from the converter thus provides values for the total pressure of steam due to the photoelastic effect on the specially shaped and dimensional sensing element.

From B-M in FIG. 4(b), sensor 4 (the still pressure P2) and sensor 5 (temperature T) are grouped together. A hollow optical fiber having an inner diameter of about 100 μm and a outer diameter of about 400 μm is made of quartz material, and said hollow optical fiber is coated with either aluminum or chromium to form an efficient infrared transmitting optical fiber. One end of this fiber is connected to the small end surface of the second sensing element 17, and the other end is connected to a thermopile detector that can be employed to measure temperatures ranging from room temperature to 450° C.

Said temperature compensation element (T1) 6 is a thermopile detector that is connected to a hollow optical fiber, and placed inside the evenly distributed tube 12.

FIG. 5 is a schematic block diagram of the electronic circuit inside the evenly distributed tube 12. A typical electronic circuit board comprises a four-layer board with a dimension of 400 mm×18 mm.

Figure 6:
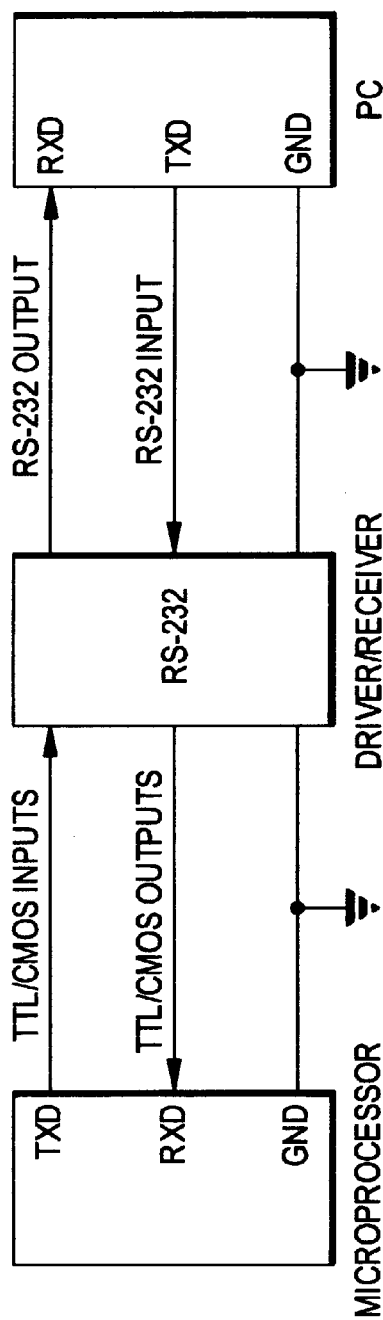
FIG. 6 shows a communication graph indicating the signal and data transfer between the apparatus and a computer outside of the well.

FIG. 6 illustrates the communication interconnection between the apparatus and the computer outside of the well.

Figure 7:
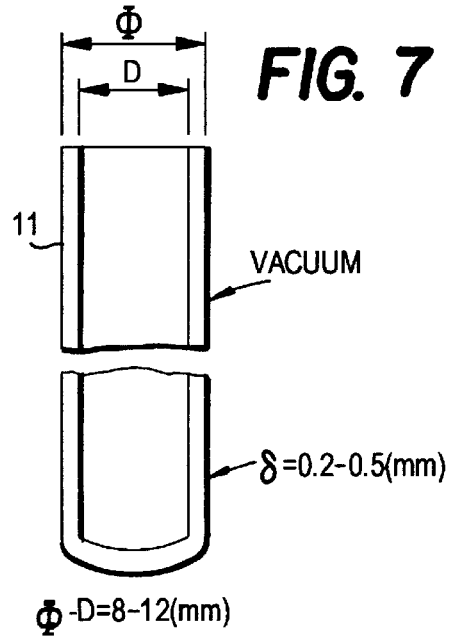
FIG. 7 is a sectional view of a thermal insulation flask.
Figure 8:
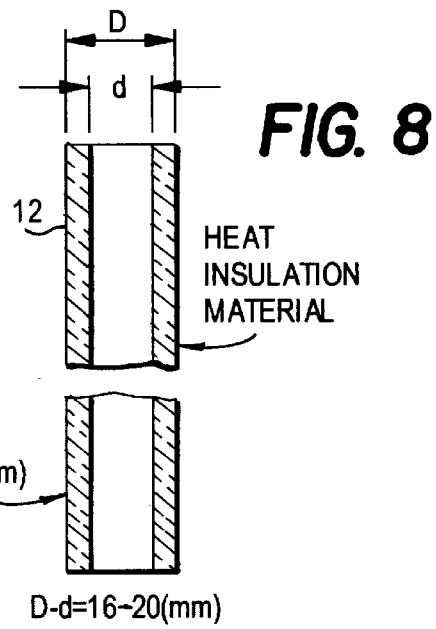
FIG. 8 is a graphical representation of a thermal well-distributed tube.

FIG. 7 shows a diagram of a thermal insulation flask 11. Said thermal insulation flask comprises two concentric cylinders, which are typically made of two smooth metal (for example, nickel or stainless steel) sheets each with a thickness about 0.20–0.50 mm. The two concentric cylinders are sealed with a vacuum-filled space of approximately 4–5 mm between them. The evenly distributed thermal tube 12 shown in FIG. 8 is inserted into the thermal insulation flask 11. A thermal insulation material 15 is filled inside the bottom of the back shell. The electronic circuit board 9, photoelectric converters, and battery are placed inside the evenly distributed thermal tube 12 for the purpose of heat insulation.

FIG. 9 shows a sectional view of a flask stopper 7. Said flask stopper 7 is used to seal the open part of the flask 11 and to allow the fibers and wires to pass through its center axis.

FIG. 10 shows a sectional view of a buffer grid 20. Said buffer grid 20 is placed inside a blind hole (to allow measurement of the still pressure P2) to avoid the flow of the steam. In order to measure the still pressure P2, i.e. to have the steam motionless, the buffer grid 20 comprises several rows of mismatched small tubes in which the steam can flow with gradually reduced speed so it finally reaches the still state at the sensor location.

Typical experiments using the sample apparatus in a downhole well demonstrate the following results.

Aridity measurement range: 0–100%
Aridity measurement error: <±0.5%
Pressure measurement range: 0–20 MPa
Pressure measurement accuracy: 0.1 MPa Temperature measurement range: 0–400° C.

Temperature measurement error: <0.5° C.

Flow rate measurement range: 0–230 m³/h

Flow rate measurement accuracy: 0.2 m³/h

Thus it may be seen that the present invention provides a feasible method and apparatus for measuring the aridity, temperature, flow rate, total pressure, still pressure, and kinetic pressure in harsh environments, which has been impossible in the past. The apparatus is very reliable, accurate, and of long-life in a harsh environment.

While the above description contains many specifications, these should not be construed as limitations on the scope of the invention, but rather as an exemplification of one preferred embodiment thereof. Many other variations are possible.

Accordingly, the scope of the invention should be determined not by the embodiments illustrated, but by the appended claims and their legal equivalents.

What is claimed is:

1. A method of determining aridity, temperature, fluid-flow rate, still pressure, kinetic pressure and the total pressure of steam at a downhole location within a steam well through which wet steam is flowing, comprising the steps of:

inserting an apparatus into said steam well;

measuring the aridity, temperature, fluid-flow rate, still pressure, kinetic pressure and the total pressure of steam with a sensing part of said apparatus that employs a sapphire or ruby, combined total pressure and aridity sensor, and a sapphire or ruby, combined still pressure and temperature sensor;

collecting and storing the data measured with an electronic circuit board and a processor inside the apparatus;

retrieving the apparatus from said well; and connecting retrieved said electronic part of the apparatus with a computer for data processing, display, printing, and storage, with software support.

2. The method of claim 1, wherein said steam well is a steam injection well.

3. The method of claim 1, wherein said steam well is a geothermal production well.

4. An apparatus for use with a method of determining aridity, temperature, fluid-flow rate, still pressure, kinetic pressure and the total pressure of steam at a downhole location within a steam well through which wet steam is flowing, comprising the steps of:

inserting an apparatus into said steam well;

measuring the aridity, temperature, fluid-flow rate, still pressure, kinetic pressure and the total pressure of steam with a sensing part of said apparatus that employs a sapphire or ruby, combined total pressure and aridity sensor, and a sapphire or ruby, combined still pressure and temperature sensor;

collecting and storing the data measured with an electronic circuit board and a processor inside the apparatus;

retrieving the apparatus from said well; and connecting retrieved said electronic part of the apparatus with a computer for data processing, display, printing, and storage, with software support, wherein said apparatus comprises:

a retriever head;
a front shell;
a back shell;
means for sensing combined total pressure and aridity;
means for sensing combined still pressure and temperature;
means for sensing kinetic pressure;
means for sensing steam flow rate;
means for heat insulation;
means for electronic communication and processing; and
a retriever socket.

5. The apparatus of claim 4, wherein said retriever head is made of stainless steel and used as a bridge to connect steel wires with the body of the apparatus;

the retriever head further serving as a means to recover the apparatus from a downhole well if the steel wires are broken.

6. The apparatus of claim 4, wherein said front shell is a hollow cylinder.

7. The apparatus of claim 4, wherein said back shell is a hollow cylinder composed of metal material selected from the group consisting of steel or aluminum, and a thermal insulation material filled into a bottom of the back shell.

8. The apparatus of claim 4, wherein said front shell and said back shell are connected with threads, and said retriever head is mounted onto the front shell.

9. The apparatus of claim 4, wherein said means for heat insulation comprises:

a thermal insulation flask comprising two concentric cylinders which are made of two polished smooth metal sheets and a sandwich layer between said two metal cylinders that is evacuated and sealed and a thermal flask stopper comprising an evenly distributed thermal tube inserted into said thermal insulation flask.

10. The apparatus of claim 4, wherein said means for sensing total pressure P1 and aridity ρ comprises:

a first light source for generating light;

a first sensing element for sensing total pressure and aridity, having a truncated cone shape with the larger end exposed to the variable condition to be sensed and the smaller end of said first sensing element oriented toward the inside of the apparatus and wherein said larger end of the first sensing element is polished into an ellipsoidal shape;

the first sensing element is interference fit to a first base, and said first base is mounted on said front shell with threads;

a first optical fiber for transmitting said first light from said first light source to said first sensing element through a polarizer;

a second optical fiber for receiving first light from said first sensing element and a second polarizer, and terminating in photoelectric converter, thus providing values for the total pressure of steam due to the photoelastic effect on the specially shaped and dimensioned sensing element;

a third optical fiber for transmitting a first light from the same first light source to the smaller end of the same sensing element; and a fourth optical fiber for transmitting said first light from the first sensing element to a photoelectric converter for providing values of the aridity of steam.

11. The apparatus of claim 6, wherein said first sensing element is a sapphire crystal.

12. The apparatus of claim 6, wherein said first sensing element is a ruby crystal.

13. The apparatus of claim 6, wherein said first sensing element further comprises at least one additional layer adhered to the larger end ellipsoid surface of the truncated cone shaped crystal to improve the sensing and anti-corrosion performance.

14. The apparatus of claim 4, wherein said means for sensing still pressure P2 and temperature T comprises:

a second light source for generating a second light;

a buffer grid comprising several rows of mismatched small tubes fabricated on the wall of the front shell and a blind hole behind said buffer grid for the purpose of having the steam inside said blind hole motionless;

a second sensing element for sensing still pressure and temperature having a truncated cone shape with the larger end exposed to the blind hole, i.e., to the variable condition to be sensed, and the smaller end of said second sensing element toward the inner part of the apparatus said larger end of the second sensing element is polished into a sphere or curved shape;

the second sensing element is interference fit to a second base, and said second base is mounted on said front shell with threads;

a fifth optical fiber for transmitting said second light from said second light source to said second sensing element through a third polarizer;

a sixth optical fiber for receiving light from said second sensing element and a fourth polarizer, and terminating in an photoelectric converter, thus providing values for the still pressure of steam due to the photoelastic effect on the second specially shaped and dimensional sensing element;

a hollow optical fiber coated with a metal connected to the small end surface of the second sensing element and terminating in a thermopile detector, providing a means for the measurement of the temperature of steam; and a temperature compensation element connected to a second hollow optical fiber, and placed inside said evenly distributed tube.

15. The apparatus of claim 13, wherein said second sensing element is a sapphire crystal.

16. The apparatus of claim 13, wherein said second sensing element is a ruby crystal.

17. The apparatus of claim 13, wherein said second sensing element further comprises at least one additional layer adhered to the larger end curved surface of the crystal to improve the sensing and anti-corrosion performance.

18. The apparatus of claim 4, wherein said means for sensing steam flow rate of the steam can thus be determined by $v^2=2(P1-P2)/\rho$, where v is the steam flow rate, P1 is the total pressure of steam, P2 is the still pressure of steam, and $\rho$ is the aridity of steam.

19. The apparatus of claim 4, wherein said means for sensing kinetic pressure P can thus be determined by $P=P1-P2$, where P1 is the total pressure of steam, and P2 is the still pressure of steam.

20. The apparatus of claim 4, wherein said means for electronic communication and processing comprises means for obtaining, processing and saving the data obtained from all the six sensors and temperature compensation element, said means for electronic communication and processing is placed inside the evenly distributed thermal tube.

21. The apparatus of claim 4 wherein said retriever socket is used to connect with a computer for the further data processing, display, printing and storage, the retriever socket is mounted with the front shell and can be separated with the back shell part.

22. The apparatus of claim 6, wherein the hollow cylinder is composed of stainless steel.

23. The apparatus of claim 14, wherein said temperature compensation element comprises a thermopile detector.

* * * * *